(12) United States Patent
Vanotti et al.

(10) Patent No.: US 8,293,762 B2
(45) Date of Patent: Oct. 23, 2012

(54) ISOQUINOLINOPYRROLOPYRIDINONES ACTIVE AS KINASE INHIBITORS

(75) Inventors: Ermes Vanotti, Milan (IT); Maria Menichincheri, Milan (IT); Alessandra Scolaro, Bresso (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 492 days.

(21) Appl. No.: 12/528,656

(22) PCT Filed: Feb. 18, 2008

(86) PCT No.: PCT/EP2008/051948
§ 371 (c)(1),
(2), (4) Date: Aug. 26, 2009

(87) PCT Pub. No.: WO2008/104475
PCT Pub. Date: Sep. 4, 2008

(65) Prior Publication Data
US 2010/0056556 A1 Mar. 4, 2010

(30) Foreign Application Priority Data
Feb. 27, 2007 (EP) .................................. 07103170.2

(51) Int. Cl.
*A61K 31/4745* (2006.01)
*C07D 471/12* (2006.01)
(52) U.S. Cl. ............. 514/287; 546/64; 546/70; 514/285
(58) Field of Classification Search .................. 514/287, 514/285; 546/64, 70
See application file for complete search history.

(56) References Cited

FOREIGN PATENT DOCUMENTS

| WO | WO 00/69846 | 11/2000 |
|----|-------------|---------|
| WO | WO 01/98299 A1 | 12/2001 |
| WO | WO 02/12242 A2 | 2/2002 |
| WO | WO 03/014090 A1 | 2/2003 |
| WO | WO 03/027114 A1 | 4/2003 |
| WO | WO 03/028720 A1 | 4/2003 |
| WO | WO 2005/009370 A2 | 2/2005 |
| WO | WO 2005/013986 A1 | 2/2005 |
| WO | WO 2005/014572 A1 | 2/2005 |
| WO | WO 2007/003611 | 1/2007 |

OTHER PUBLICATIONS

Blache Y. et al., "Reactivity of Heterocyclic Enaminones: Regioselective Synthesis of Polyfused Indolones", *Heterocycles* 53(4):905-916 (2000).
Ferlin M.G. et al., "Synthesis and Biological Properties of a New Series of N-Pyrido Substituted Tetrahydrocarbazoles", *Il Farmaco* 53(6):431-437 (1998).
Cohen P., "The Development and Therapeutic Potential of Protein Kinase Inhibitors", *Current Opinion in Chemical Biology* 3:459-465 (1999).
Montagnoli A. et al., "Drf1, a Novel Regulatory Subunit for Human Cdc7 Kinase", *The EMBO Journal* 21(12):3171-3181 (2002).
Montagnoli A. et al., "Cdc7 Inhibition Reveals a p53-Dependent Replication Checkpoint that is Defective in Cancer Cells", *Cancer Research* 64:7110-7116 (2004).

*Primary Examiner* — Charanjit Aulakh
(74) *Attorney, Agent, or Firm* — Scully, Scott, Murphy & Presser, P.C.

(57) ABSTRACT

Heteroarylpyridinone derivatives represented by formula (I)

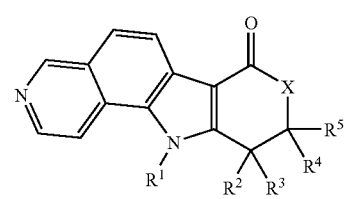

(I)

wherein $R^1$, $R^2$, $R^3$, $R^4$, $R^5$, and X are as defined in the specification, compositions thereof, and methods of use thereof. Particularly, there are described isoquinolinoyrrolopyridinones, pharmaceutical compositions including them and their use as therapeutic agents in the treatment of cancer and cell proliferation disorders.

13 Claims, No Drawings

ISOQUINOLINOPYRROLOPYRIDINONES ACTIVE AS KINASE INHIBITORS

FIELD OF THE INVENTION

The present invention relates to isoquinolinpyrrolopyridinones, to pharmaceutical compositions comprising them and to their use as therapeutic agents, particularly in the treatment of cancer and cell proliferation disorders.

BACKGROUND OF THE INVENTION

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis. PKs are also implicated in inflammatory conditions and in the multiplication of viruses and parasites. PKs can also play a major role in the pathogenesis and development of neurodegenerative disorders. PKs malfunctioning and disregulation are further discussed in Current Opinion in Chemical Biology 1999, 3, 459-465.

Among the several protein kinases known in the art as being implicated in the growth of cancer cells is Cdc7, an evolutionary conserved serine-threonine kinase which plays a pivotal role in linking cell cycle regulation to genome duplication, being essential for the firing of DNA replication origins (see Montagnoli A. et al., EMBO Journal, Vol. 21, No. 12, pp. 3171-3181, 2002; Montagnoli A. et al., Cancer Research Vol. 64, October 1, pp. 7110-7116, 2004).

Blache, et al. in Heterocycles (2000), 53(4), 905-916, describe a regioselective synthesis of polyfused indolones, in particular there is disclosed a compound named 7H-pyrido[4,3-a]carbazol-7-one, 8,9,10,11-tetrahydro-11-(phenylmethyl).

Several heterocyclic compounds are known in the art as protein kinase inhibitors. Among them are, for instance, pyridinylpyrroles disclosed in WO 2005/13986, pyrimidinylpyrroles disclosed in WO 2005/14572, pyrrolo-pyrazoles disclosed in WO 02/12242; tetrahydroindazoles disclosed in WO 00/69846; pyrrolo-pyridines disclosed in WO 01/98299; aminophthalazinones disclosed in WO 03/014090 and aminoindazoles disclosed in WO 03/028720.

Beta-carbolines and analogs for use as mitogen-activated protein kinase-activated protein kinase-2 inhibitors, such as 7H-pyrido[3',4':4,5]pyrrolo[2,3-f]isoquinolin-7-one, 8,9,10,11-tetrahydro, are described and claimed in WO 2005/009370.

In addition, pyrrolopyridinone derivatives for the treatment of obesity are disclosed in the patent WO03/027114 to Bayer Pharmaceuticals Corporation. In particular a pyridylpyrrolopyridinone, namely 5-cyclohexyl-1-(2,4-dichloro-phenyl)-3-methyl-2-pyridin-3-yl-1,5,6,7-tetrahydro-pyrrolo[3,2-c]pyridin-4-one is reported.

Pyrrolopyridinone derivatives, endowed with mitogen activated protein kinase-activated protein kinase-2 inhibitory activity, are disclosed in the patent application WO2004/058762 A1 to Pharmacia Corp.

SUMMARY OF THE INVENTION

The invention relates to novel compounds which are useful, in therapy, as agents against a host of diseases caused by and/or associated to a disregulated protein kinase activity and, more particularly, Cdk2 and Cdc7 activity.

The invention also relates to compounds which have protein kinase inhibiting activity and, more particularly, Cdk2 and Cdc7 inhibiting activity.

One aspect of the invention relates to heteroarylpyridinone derivatives which are represented by formula (I)

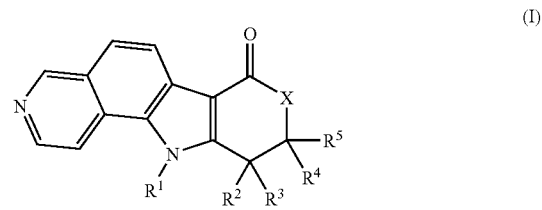

wherein
$R^1$ is selected from the group consisting of hydrogen, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)haloalkyl, ($C_1$-$C_6$)polyfluorinated alkyl, heterocyclyl, aryl, heteroaryl, ($C_3$-$C_6$)cycloalkyl-($C_1$-$C_6$)alkyl, heterocyclyl-($C_1$-$C_6$)alkyl, aryl-($C_1$-$C_6$)alkyl, heteroaryl-($C_1$-$C_6$)alkyl, ($C_1$-$C_8$)hydroxyalkyl, ($C_1$-$C_8$)alkoxy-($C_1$-$C_8$)alkyl, aryloxy-($C_1$-$C_8$)alkyl, heteroaryloxy-($C_1$-$C_8$)alkyl, ($C_1$-$C_8$)aminoalkyl, ($C_1$-$C_8$)alkylamino-($C_1$-$C_8$)alkyl, ($C_1$-$C_8$)dialkylamino-($C_1$-$C_8$)alkyl, carbamoyl-($C_1$-$C_8$)alkyl, and alkoxycarbonyl, wherein each of said aryl, heteroaryl, heterocyclyl, aryloxy, or heteroaryloxy moieties can be unsubstituted or substituted by one or more substituents, each substituent being independently selected from the group consisting of alkyl, aryl, —$OCF_3$, —OC(O)alkyl, —OC(O)aryl, —$CF_3$, heteroaryl, aralkyl, alkylaryl, heteroaralkyl, alkylheteroaryl, hydroxy, hydroxyalkyl, alkoxy, aryloxy, aralkoxy, acyl, aryl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, heterocyclyl, heterocyclenyl, —NH(alkyl), —NH(cycloalkyl), and —N(alkyl)$_2$;

$R^2$, $R^3$, $R^4$ and $R^5$ are each independently selected from the group consisting of hydrogen atom, ($C_1$-$C_6$)alkyl, ($C_3$-$C_6$)cycloalkyl, heterocyclyl, aryl, cycloalkyl-alkyl, heterocyclyl-($C_1$-$C_6$)alkyl, aryl-($C_1$-$C_6$)alkyl, ($C_1$-$C_6$)haloalkyl, ($C_1$-$C_6$)polyfluorinated alkyl, ($C_1$-$C_8$)hydroxyalkyl, ($C_1$-$C_8$)alkoxy-($C_1$-$C_8$)alkyl, aryloxy($C_1$-$C_8$)alkyl, heteroaryloxy($C_1$-$C_8$)alkyl, ($C_1$-$C_8$)aminoalkyl, ($C_1$-$C_8$)alkylamino($C_1$-$C_8$)alkyl, and ($C_1$-$C_8$)dialkylamino-($C_1$-$C_8$)alkyl,
or $R^2$, $R^3$, $R^4$ and $R^5$, taken together, form a ($C_3$-$C_6$)cycloalkyl group;
X is NH or $CH_2$,
with the provisos that,
when X is NH and $R^1$ is hydrogen atom, at least one of $R^2$, $R^3$, $R^4$ and $R^5$ is not a hydrogen atom and
7H-pyrido[4,3-a]carbazol-7-one, 8,9,10,11-tetrahydro-11-(phenylmethyl) is excluded;
or a pharmaceutically acceptable salt for solvate thereof.

Another aspect of the invention relates to a method of treating cell proliferative disorders or conditions, that can be caused by and/or associated with an altered protein kinase activity, by administering to a mammal in need of said treatment an amount of a compound of Formula (I).

Another aspect of the invention relates to a method of antagonizing activity toward Cdk2 or Cdc7, comprising administering to said Cdk2 or Cdc7 an amount of a compound of Formula (I) that is effective in antagonizing activity toward Cdk2 or Cdc7.

Another aspect of the invention relates to a method of treating a disorder or condition in a mammal, wherein antagonist activity toward toward Cdk2 or Cdc7 is needed in said mammal, comprising administering to said mammal an amount of a compound of Formula (I) that is effective in antagonizing activity toward Cdk2 or Cdc7.

Another aspect of the invention relates to a method of treating a disorder or condition in a mammal for which antagonist activity toward toward Cdk2 or Cdc7 is needed in said mammal, comprising administering to said mammal an amount of a compound of Formula (I) that is effective in treating said disorder or condition.

Another aspect of the invention relates to a method of treating a disorder or condition selected from the group consisting of bladder cancer, breast cancer, colon cancer, kidney cancer, liver cancer, lung cancer, including small cell lung cancer, esophagus cancer, gall-bladder cancer, ovarian cancer, pancreatic cancer, stomach cancer, cervical cancer, thyroid cancer, prostate cancer, and skin cancer, including squamous cell carcinoma, hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma, Burkitt's lymphoma, hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma, in a mammal, comprising administering to said mammal in need of said treatment an amount of a compound of Formula (I) that is effective in treating said condition or disorder.

Another aspect of the invention relates to a method of treating a disorder or condition selected from the group consisting of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis, in a mammal, comprising administering to said mammal in need of said treatment an amount of a compound of Formula (I) that is effective in treating said condition or disorder.

Another aspect of the invention relates to a method of treating a disorder or condition selected from the group consisting of bladder cancer, breast cancer, colon cancer, kidney cancer, liver cancer, lung cancer, including small cell lung cancer, esophagus cancer, gall-bladder cancer, ovarian cancer, pancreatic cancer, stomach cancer, cervical cancer, thyroid cancer, prostate cancer, and skin cancer, including squamous cell carcinoma, hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma, Burkitt's lymphoma, hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma, in a mammal, comprising administering to said mammal in need of said treatment an amount of a compound of Formula (I) that is effective in antagonizing activity toward Cdk2 or Cdc7.

Another aspect of the invention relates to a method of treating a disorder or condition selected from the group consisting of benign prostate hyperplasia, familial adenomatosis, polyposis, neuro-fibromatosis, psoriasis, vascular smooth cell proliferation associated with atherosclerosis, pulmonary fibrosis, arthritis glomerulonephritis, post-surgical stenosis and restenosis, in a mammal, comprising administering to said mammal in need of said treatment an amount of a compound of Formula (I) that is effective in antagonizing activity toward Cdk2 or Cdc7.

Another aspect of the invention relates to a pharmaceutical composition comprising an amount of the compound of Formula (I), or a pharmaceutically acceptable salt thereof, and a pharmaceutically acceptable carrier.

Preferably, specific types of cancer that can be treated from those listed above include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer, and Kaposi's sarcoma.

A more complete appreciation of the invention, and many of the attendant advantages thereof, will be readily understood as the same becomes better understood by reference to the following detailed description.

DETAILED DESCRIPTION OF THE INVENTION

One aspect of the invention relates to heteroarylpyridinone derivatives which are represented by formula (I)

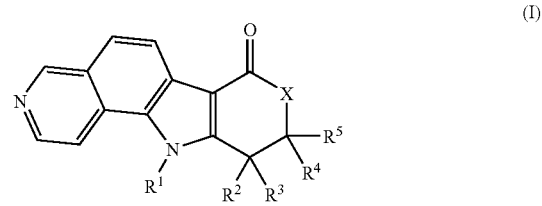

wherein $R^1$ is selected from the group consisting of hydrogen, $(C_1\text{-}C_6)$alkyl, $(C_2\text{-}C_6)$alkenyl, $(C_2\text{-}C_6)$alkynyl, $(C_3\text{-}C_6)$cycloalkyl, $(C_1\text{-}C_6)$haloalkyl, $(C_1\text{-}C_6)$polyfluorinated alkyl, heterocyclyl, aryl, heteroaryl, $(C_3\text{-}C_6)$cycloalkyl-$(C_1\text{-}C_6)$ alkyl, heterocyclyl-$(C_1\text{-}C_6)$alkyl, aryl-$(C_1\text{-}C_6)$alkyl, heteroaryl-$(C_1\text{-}C_6)$alkyl, $(C_1\text{-}C_8)$hydroxyalkyl, $(C_1\text{-}C_8)$alkoxy-$(C_1\text{-}C_8)$alkyl, aryloxy-$(C_1\text{-}C_8)$alkyl, heteroaryloxy-$(C_1\text{-}C_8)$alkyl, $(C_1\text{-}C_8)$aminoalkyl, $(C_1\text{-}C_8)$alkylamino-$(C_1\text{-}C_8)$alkyl, $(C_1\text{-}C_8)$dialkylamino-$(C_1\text{-}C_8)$alkyl, carbamoyl-$(C_1\text{-}C_8)$ alkyl, and alkoxycarbonyl, wherein each of said aryl, heteroaryl, heterocyclyl, aryloxy, or heteroaryloxy moieties can be unsubstituted or substituted by one or more substituents, each substituent being independently selected from the group consisting of alkyl, aryl, —$OCF_3$, —OC(O)alkyl, —OC(O) aryl, —$CF_3$, heteroaryl, aralkyl, alkylaryl, heteroaralkyl, alkylheteroaryl, hydroxy, hydroxyalkyl, alkoxy, aryloxy, aralkoxy, acyl, aryl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, heterocyclyl, heterocyclenyl, —NH(alkyl), —NH(cycloalkyl), and —N(alkyl)$_2$;

$R^2$, $R^3$, $R^4$ and $R^5$ are each independently selected from the group consisting of hydrogen atom, $(C_1$-$C_6)$alkyl, $(C_3$-$C_6)$cycloalkyl, heterocyclyl, aryl, cycloalkyl-alkyl, heterocyclyl-$(C_1$-$C_6)$alkyl, aryl-$(C_1$-$C_6)$alkyl, $(C_1$-$C_6)$haloalkyl, $(C_1$-$C_6)$polyfluorinated alkyl, $(C_1$-$C_8)$hydroxyalkyl, $(C_1$-$C_8)$alkoxy-$(C_1$-$C_8)$alkyl, aryloxy$(C_1$-$C_8)$alkyl, heteroaryloxy$(C_1$-$C_8)$alkyl, $(C_1$-$C_8)$aminoalkyl, $(C_1$-$C_8)$alkylamino$(C_1$-$C_8)$alkyl, and $(C_1$-$C_8)$dialkylamino-$(C_1$-$C_8)$alkyl, or $R^2$, $R^3$, $R^4$ and $R^5$, taken together, form a $(C_3$-$C_6)$cycloalkyl group;

X is NH or $CH_2$, with the proviso that, when X is NH and $R_1$ is hydrogen atom, at least one of $R^2$, $R^3$, $R^4$ and $R^5$ is not a hydrogen atom;

or a pharmaceutically acceptable salt for solvate thereof.

The compounds of formula (I) of the invention can have asymmetric carbon atoms and can therefore exist as individual optical isomers, as racemic admixtures or as any other admixture including a majority of one of the two optical isomers, which are all to be intended as comprised within the scope of the present invention.

Likewise, the use as an antitumor agent of all the possible isomers and their admixtures and of both the metabolites and the pharmaceutically acceptable bio-precursors (otherwise referred to as pro-drugs) of the compounds of formula (I) are also within the scope of the present invention. Prodrugs are any covalently bonded compounds which release the active parent drug, according to formula (I), in vivo.

In cases when compounds can exist in tautomeric forms, for instance keto-enol tautomers, each tautomeric form is contemplated as being included within this invention whether existing in equilibrium or predominantly in one form.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkylamino", "dialkylamino" etc.

As used above, and throughout the specification, the following terms, unless otherwise indicated, shall be understood to have the following meanings:

"Mammal" means humans and other animals.

"Treating" refers to, and includes, reversing, alleviating, inhibiting the progress of, or preventing, a disease, disorder or condition, or one or more symptoms thereof; and, "treatment" and "therapeutically" refer to the act of treating, as defined above.

The term "effective amount" means an amount of compound of the present invention that is capable of treating a specific disease or antagonizing a specific enzyme, such as a specific protein kinase. The particular dose of compound administered according to the invention will be determined by the particular circumstances surrounding the case including, for example, the compound administered, the route of administration, the state of being of the subject, and the severity of the pathological condition being treated.

"Alkyl" means an aliphatic hydrocarbon group, which can be straight or branched. $(C_1$-$C_6)$alkyl means an alkyl group that is 1-6 carbon atoms long. Branched means that one or more alkyl groups, such as methyl, ethyl or propyl, are attached to a linear alkyl chain. Nonlimiting examples of alkyl groups include methyl, ethyl, n-propyl, isopropyl, n-butyl, isobutyl, tert-butyl, sec-butyl, n-pentyl, n-hexyl, and the like. The alkyl group can be substituted by one or more substituents which can each be independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, and t-butyl, isobutyl, sec-butyl, n-pentyl, n-hexyl, and the like.

"Alkenyl" means an aliphatic hydrocarbon group containing at least one carbon-carbon double bond and which can be straight or branched. $(C_2$-$C_6)$alkenyl means an alkenyl group that is 2-6 carbon atoms long. The term "substituted alkenyl" means that the alkenyl group can be substituted by one or more substituents which can be the same or different, each substituent being independently selected from the group consisting of halo, alkyl, aryl, cycloalkyl, cyano, and alkoxy. Non-limiting examples of suitable alkenyl groups include ethenyl, propenyl, and n-butenyl.

"Alkynyl" means an aliphatic hydrocarbon group containing at least one carbon-carbon triple bond and which can be straight or branched. $(C_2$-$C_6)$alkynyl means an alkynyl group that is 2-6 carbon atoms long. Branched means that one or more lower alkyl groups such as methyl, ethyl or propyl, are attached to a linear alkynyl chain. Non-limiting examples of suitable alkynyl groups include ethynyl, propynyl, and 2-butynyl. The term "substituted alkynyl" means that the alkynyl group can be substituted by one or more substituents each being independently selected from the group consisting of alkyl, aryl and cycloalkyl.

"amino" means an —$NH_2$ group whilst the term arylamino comprises any group —NH-aryl, wherein aryl is as defined below.

"halogen" or "halo" means a fluorine, chlorine, bromine or iodine atom.

"polyfluorinated alkyl" means any alkyl group as defined above being substituted by two or more fluorine atoms such as, for instance, trifluoromethyl, 2,2,2-trifluoroethyl, 3,3,3-trifluoropropyl, 1,1-difluoroethyl, 3,3-difluoropropyl and the like.

With the term aryl the present invention contemplates any carbocyclic or heterocyclic hydrocarbon with from 1 to 2 ring moieties, either fused or linked to each other by single bonds, wherein at least one of the rings is aromatic. If present, any aromatic heterocyclic hydrocarbon also referred to as heteroaryl group, comprises a 5 to 6 membered ring with from 1 to 3 heteroatoms selected among N, O or S.

The aryl group can be unsubstituted or substituted on the ring with one or more substituents, each being independently selected from the group consisting of alkyl, aryl, —$OCF_3$, —OC(O)alkyl, —OC(O)aryl, —$CF_3$, heteroaryl, aralkyl, alkylaryl, heteroaralkyl, alkylheteroaryl, hydroxy, hydroxyalkyl, alkoxy, aryloxy, aralkoxy, acyl, aryl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, heterocyclyl, heterocyclenyl, —NH(alkyl), —NH(cycloalkyl), and —N(alkyl)$_2$. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like. Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like.

"cycloalkyl" means a non-aromatic mono- or multicyclic ring system. ($C_3$-$C_6$)cycloalkyl means a cycloalkyl group that is 3-6 carbon atoms long. The cycloalkyl can be optionally substituted on the ring by replacing an available hydrogen on the ring by one or more substituents, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aryl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, —NH(alkyl), —NH(cycloalkyl), and —N(alkyl)$_2$. Non-limiting examples of suitable monocyclic cycloalkyls include cyclopropyl, cyclobutyl, cyclopentyl and cyclohexyl.

"heterocyclyl" means any 5 or 6 membered heterocyclic ring comprising from 1 to 3 heteroatoms selected among N, O or S. If the said heterocycle or heterocyclyl group is an aromatic heterocycle, also referred to as heteroaryl, it is encompassed by the above definition given to aryl groups.

As such, besides the above aromatic heterocycles, the term heterocyclyl also encompasses saturated or partially unsaturated heterocycles such as, for instance, pyrroline, pyrrolidine, imidazoline, imidazolidine, pyrazoline, pyrazolidine, piperidine, piperazine, morpholine, and the like.

In this respect, as an example, any group which is identified as an arylalkyl has to be intended as an alkyl group which is further substituted by aryl, wherein both aryl and alkyl are as above defined. Clearly when $R^2$ and $R^3$ or $R^4$ and $R^5$, taken together, form a ($C_3$-$C_6$)cycloalkyl group, the compound is referred to as spiro derivative.

When the aryl or heteroaryl group is optionally substituted, the substituents are chosen from alkyl, haloalkyl, polyfluoroalkyl, hydroxyalkyl, aminoalkyl, amino, alkylamino, dialkylamino, cyano, hydroxy, alkoxy, halogen, as herein defined.

Pharmaceutically acceptable salts of the compounds of formula (I) include the acid addition salts with inorganic or organic acids such as, for instance, nitric, hydrochloric, hydrobromic, sulfuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid.

Prodrugs and solvates of the compounds of the invention are also contemplated herein. The term "prodrug", as employed herein, denotes a compound that is a drug precursor, which, upon administration to a subject, undergoes chemical conversion by metabolic or chemical processes to yield a compound of formula (I) or a salt and/or solvate thereof. A discussion of prodrugs is provided in T. Higuchi and V. Stella, Prodrugs as Novel Delivery Systems (1987) Volume 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

When any variable (e.g., aryl, alkyl, etc.) occurs more than one time in any constituent or in Formula (I), its definition on each occurrence is independent of its definition at every other occurrence. Also, combinations of substituents and/or variables are permissible only if such combinations result in stable compounds.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkylamino", "dialkylamino" etc.

A preferred class of compounds of the invention is represented by the derivatives of formula (I) wherein X, $R^1$, $R^2$, and $R^3$ are as defined above and both $R^4$ and $R^5$ are hydrogen atoms.

Another preferred class of compounds of the invention is represented by the derivatives of formula (I) wherein X, $R^1$, $R^4$ and $R^5$ are as defined above and both $R^2$ and $R^3$ are hydrogen atoms.

Another preferred class of compounds of the invention is represented by the derivatives of formula (I) wherein $R^1$, $R^2$, $R^3$ and $R^4$ are hydrogen atoms.

Another preferred class of compounds of the invention is represented by the derivatives of formula (I) wherein $R^1$, $R^2$, $R^3$ and $R^4$ are hydrogen atoms.

More preferred class of compounds of the invention is represented by the derivatives of formula (I) wherein X is NH, $R^1$, $R^2$, $R^4$ and $R^5$ are hydrogen atoms.

The compounds of formula (I) can be obtained from the following schemes which are described in detail hereinbelow:

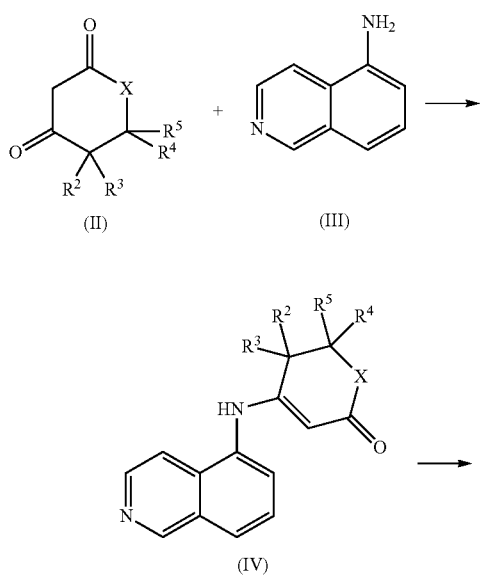

SCHEME 1 (compounds I)

-continued

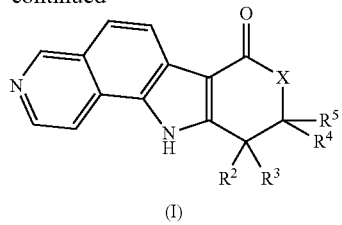

(I)

For a reference to any specific compound of formula (I) of the invention, optionally in the form of a pharmaceutically acceptable salt, see the experimental section and claims.

The compounds of formula (I) and the pharmaceutically acceptable salts thereof can be obtained by a process according to SCHEME 1 comprising:

a) reacting derivatives of formula (II) with isoquinolin-5-ylamine (III) so to obtain a compound of formula (IV)

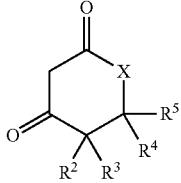

(II)

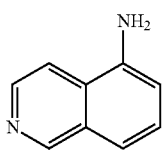

(III)

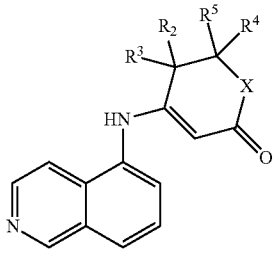

(IV)

wherein X, $R^2$, $R^3$, $R^4$ and $R^5$ are as above defined;

b) cyclizing compound (IV) via carbon-carbon bond formation so as to obtain the desired compound of formula (I), where $R_1$ is a hydrogen atom, and, optionally, converting it into another compound of formula (I) and/or into a pharmaceutically acceptable salt thereof.

This reaction can be obtained according to well known procedures described in the literature, for instance, performing the reaction by heating compound (IV) in a suitable solvent, such as N,N-dimethylformamide (DMF), in the presence of palladium diacetate and copper diacetate, at a temperature ranging from about 80 to about 150° C. for a period of time ranging from about one hour to several hours.

SCHEME 2 (compounds I)

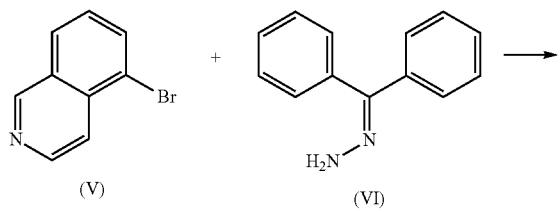

-continued

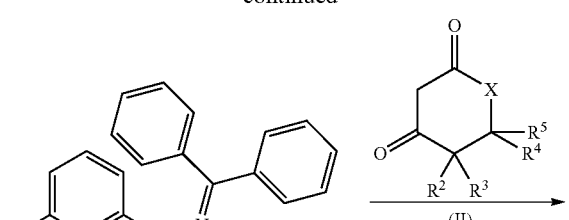

(VII)

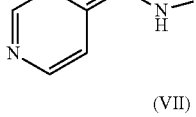

(II)

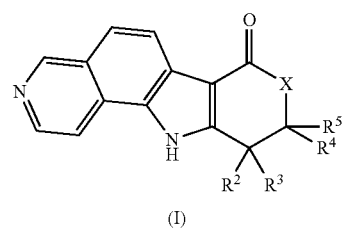

(I)

In the alternative, the compounds of formula (I) can be synthesized by a route according to SCHEME 2 comprising:

a) reacting 5-bromoisoquinoline (V) and benzhydrylidene-hydrazine (VI) to give N-benzhydrylidene-N'-isoquinolin-5-yl-hydrazine (VII).

(V)

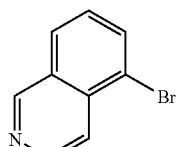

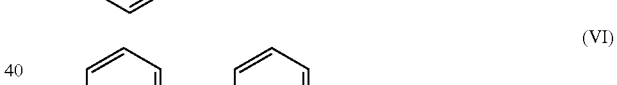

(VI)

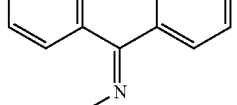

(VII)

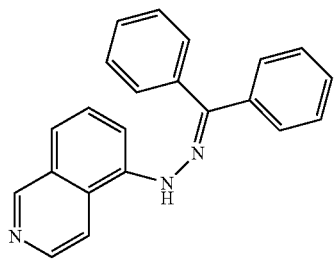

b) reacting compound (VII) with compounds of formula (II) so as to obtain the compounds of formula (I), where $R_1$ is a hydrogen atom. If enolizable not symmetrical compounds of formula (II) are employed in this reaction, the formation of variable amounts of regioisomers might be observed.

The compounds of formula (II), (III), (V), (VI) in SCHEMES 1 and 2, as well as any other reactant of the process, are known or, if not commercially available per se, can be easily prepared according to known methods.

SCHEME 3A (Compounds II)

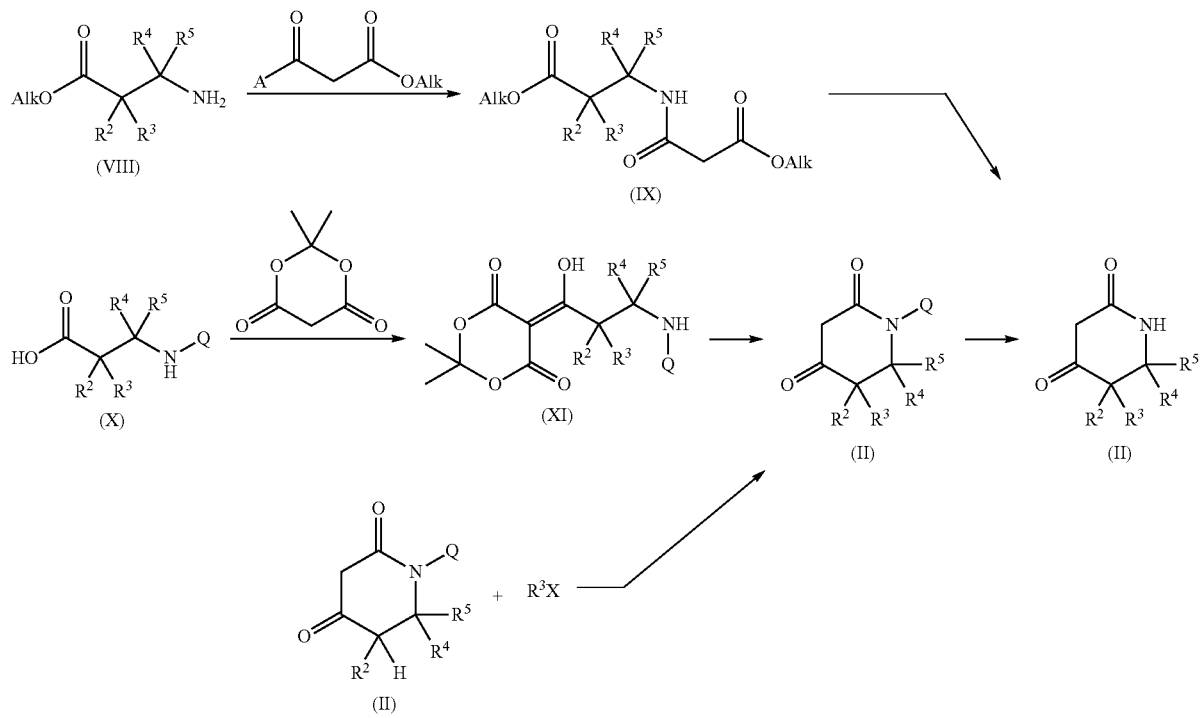

In SCHEME 3A, Piperidine-dione derivatives (II) are known compounds or, alternatively, can be prepared by known methods, for instance, when X is NH, according to the synthetic pathway below, wherein Alk stands for a suitable lower alkyl group, e.g. ethyl, and A stands for chloro or OAlk:

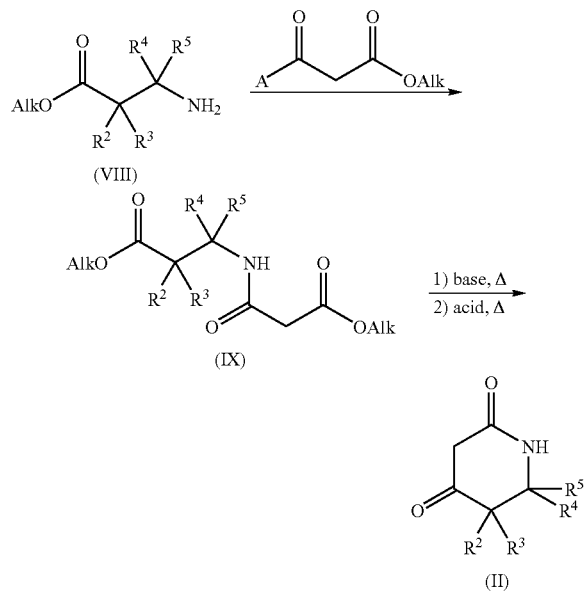

In this respect, a suitable β-amino-carboxyester (VIII) derivative, wherein $R^2$, $R^3$, $R^4$ and $R^5$ have the above reported meanings, is reacted with dialkylmalonate or, alternatively, with 3-chloro-3-oxopropanoic acid alkyl ester, for instance, dimethylmalonate or ethyl 3-chloro-3-oxopropanoate, respectively. When A is chloro, the reaction is carried out under basic conditions, for instance in the presence of triethylamine, and in a suitable solvent such as dichloromethane, at a temperature ranging from about room temperature to about reflux temperature. When A is OAlk, the reaction is carried out with or without basic conditions and more conveniently in the absence of solvents at a reflux temperature of the dialkylmalonate.

When not commercially available, the above mentioned β-amino-carboxyester derivatives (VIII) can be obtained according to well known procedures described in the literature.

The intermediate derivative (IX) thus obtained is then converted into the compound of formula (II), first by reacting it under basic conditions, e.g. in the presence of sodium methylate and a suitable solvent, preferably toluene, at refluxing temperature and for a time ranging from about 2 hours to about 24 hours. Subsequently, the product of the former step is reacted as such, without being isolated, with an acetonitrile/water/acetic acid mixture under refluxing conditions and for a time varying between about 6 hours and about 24 hours.

In the alternative, the piperidine-dione derivative (II) can be prepared, for instance, according to the synthetic pathway below:

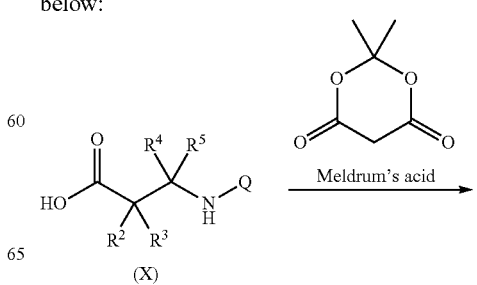

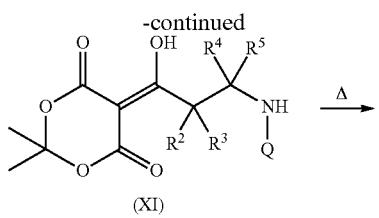

(XI)

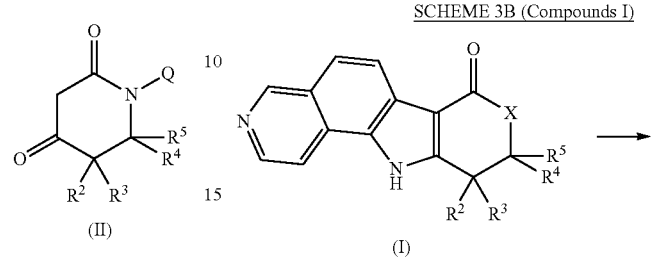

In the procedure, Meldrum's acid is reacted with a suitable aminoacid derivative of formula (X) so as to obtain a compound of formula (XI) wherein Q is a suitable nitrogen protecting group, such as, in particular, tert-butoxycarbonyl, or other groups, for example, p-methoxyphenyl, wherein $R^2$, $R^3$, $R^4$ and $R^5$ are as defined above. The compound of formula (XI) is then cyclized by dissolving it in a suitable solvent, for instance ethyl acetate, and refluxing for a period of time ranging from about 1 hour to about 24 hours.

The aminoacid derivative (X) is a known compound or, alternatively, can be prepared by known methods, according to well known procedures described in the literature.

In the alternative, the piperidine-dione derivative (II) can be modified according to the synthetic pathway below, wherein Q is as above defined, X is halide, triflate, mesylate, tosylate and the like, and $R^3$ is as defined above:

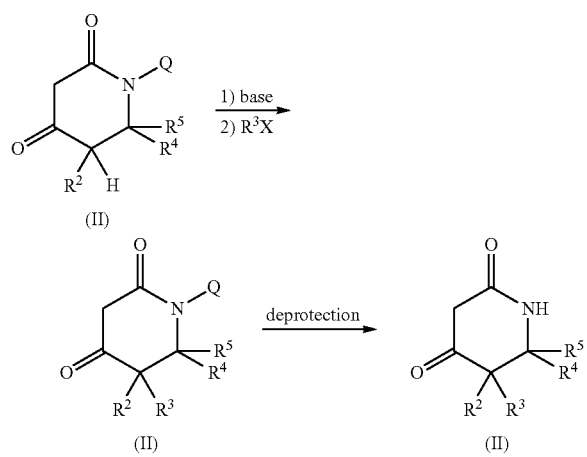

In this respect, a suitable piperidine-dione derivative (II), wherein $R^2$, $R^4$ and $R^5$ have the above reported meanings, but are preferentially hydrogen atoms, is reacted with a base, for instance lithium bis(trimethylsilyl)amide (LiHMDS). The reaction is carried out in a suitable solvent such as tetrahydrofuran, at a temperature comprised between −78° C. and room temperature.

The reaction mixture is then treated with a suitable $R^3X$, wherein X is a group such as halide, triflate, mesylate, tosylate and the like, thus obtaining another compound of formula (II). The compound thus obtained can be converted into another compound of formula (II) by treating it, for instance, when Q is tert-butoxycarbonyl group, with acidic conditions, e.g. in the presence of trifluoroacetic acid and of a suitable solvent, preferably dichloromethane. The reaction can be carried out at room temperature and for a time ranging from about 1 hour to about 6 hours.

SCHEME 3B (Compounds I)

In SCHEME 3B, the compounds of formula (I), where $R^1$ is different from hydrogen, can be obtained by different general procedures, for instance, by derivatization of the pyrrole nitrogen atom, reacting them with electrophiles of formula $R^1$—X, wherein X is halide, triflate, mesylate, tosylate and the like, so that a compound of formula (I), bearing $R^1$ as defined, is obtained.

As discussed above, the compounds of formula (I), wherein $R^1$ is as defined, can be prepared by reacting the isoquinolinopyrrolopyridinone of formula (I), wherein $R^1$ is a hydrogen atom, with a suitable electrophile, such as a convenient halide or a triflate, in a suitable solvent, such as N,N-dimethylformamide, tetrahydrofuran, dioxane, in the presence of a suitable base, such as sodium hydride. The reaction can be carried out at a temperature ranging from about −30° C. to about room temperature, preferably at 0° C. for a for a period of time ranging from about 1 hour to 24 hours.

Alternatively, a different base can be used, for instance potassium or cesium carbonate, optionally in the presence of a crown ether, for example 18-crown-6, in a suitable solvent, such as DMF. The reaction can be carried out at temperatures ranging from about room temperature to about 100° C., optionally in a microwave cavity.

Likewise, the conversion of a compound of formula (I) into a pharmaceutically acceptable salt is easily carried out according to known methods, e.g. by contacting any free base of formula (I) with any suitable pharmaceutically acceptable acid.

From all of the above, it would be clear to the skilled person that when preparing the compounds of formula (I) according to the aforementioned processes, comprehensive of any variant thereof, optional functional groups within the starting materials or the intermediates thereof and which could give rise to unwanted side reactions, need to be properly protected according to conventional techniques. Likewise, the conversion of these latter into the free deprotected compounds can be carried out according to known procedures.

By analogy, any compound of formula (I) which is susceptible of being salified can be easily converted into the corresponding acid addition salt, by working in the presence of any pharmaceutically acceptable acid, for instance selected among those previously reported.

As it will be readily appreciated, if the compounds of formula (I) prepared according to the process described above are obtained as a mixture of isomers, their separation into the single isomers of formula (I), according to conventional techniques, is also within the scope of the present invention.

Conventional techniques for racemate resolution include, for instance, partitioned crystallization of diastereoisomeric salt derivatives or preparative chiral HPLC.

Pharmacology

The compounds of formula (I) are active as protein kinase inhibitors and are therefore useful, for instance, to restrict the unregulated proliferation of tumor cells. In therapy, they can be used in the treatment of various tumors, such as those formerly reported, as well as in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative Cdc7 inhibitors and the potency of selected compounds is determined through a method of assay based on the use of Dowex resin capture technology.

The assay consists of the transfer of radioactivity labeled phosphate moiety by the kinase to an acceptor substrate. The resulting 33P-labeled product is separated from unreacted tracer, transferred into a scintillation cocktail and light emitted is measured in a scintillation counter.

Inhibition Assay of Cdc7 Activity

The inhibiting activity of putative Cdc7 inhibitors and the potency of selected compounds is determined through a method of assay based on the use of Dowex resin capture technology.

The assay consists of the transfer of radioactivity labeled phosphate moiety by the kinase to an acceptor substrate. The resulting 33P-labeled product is separated from unreacted tracer, transferred into a scintillation cocktail and light emitted is measured in a scintillation counter.

The inhibition assay of Cdc7/Dbf4 activity is performed according to the following protocol.

The MCM2 substrate is trans-phosphorylated by the Cdc7/Dbf4 complex in the presence of ATP traced with $\gamma^{33}$-ATP. The reaction is stopped by addition of Dowex resin in the presence of formic acid. Dowex resin particles capture unreacted $\gamma^{33}$-ATP and drag it to the bottom of the well while $^{33}$P phosphorylated MCM2 substrate remains in solution. The supernatant is collected, transferred into Optiplate plates and the extent of substrate phosphorylation is evaluated by $\beta$ counting.

The inhibition assay of Cdc7/Dbf4 activity was performed in 96 wells plate according to the following protocol.

To each well of the plate were added:
- 10 μl test compound (10 increasing concentrations in the nM to uM range to generate a dose-response curve). The solvent for test compounds contained 3% DMSO. (final concentration 1%)
- 10 μl substrate MCM2 (6 mM final concentration), a mixture of cold ATP (2 mM final concentration) and radioactive ATP (1/5000 molar ratio with cold ATP).
- 10 μl enzyme (Cdc7/Dbf4, 2 nM final concentration) that started the reaction. The buffer of the reaction consisted in 50 mM HEPES pH 7.9 containing 15 mM $MgCl_2$, 2 mM DTT, 3 uM $NaVO_3$, 2 mM glycerophosphate and 0.2 mg/ml BSA.

After incubation for 60 minutes at room temperature, the reaction was stopped by adding to each well 150 μl of Dowex resin in the presence of 150 mM formic acid.

After another 60 min incubation, 50 μL of suspension were withdrawn and transferred into 96-well OPTI-PLATEs containing 150 μl of MicroScint 40 (Packard); after 5-10 minutes shaking the plates were read for 1 min in a Packard TOP-Count radioactivity reader. $IC_{50}$ determination: inhibitors were tested at different concentrations ranging from 0.0005 to 10 μM. Experimental data were analyzed by the computer program Assay Explorer using the four parameter logistic equation:

$$y = \text{bottom} + (\text{top}-\text{bottom})/(1+10^{((\log IC_{50}-x)*\text{Slope})})$$

where x is the logarithm of the inhibitor concentration, y is the response; y starts at bottom and goes to top with a sigmoid shape.

In addition the selected compounds have been characterized for specificity on Cdk2A, on a panel of ser/threo kinases strictly related to cell cycle (Cdk2/cyclin E, Cdk1/cyclin B1, Cdk4/Cyclin D1, Cdk5/p25), on IGF1-R, Aurora-2, AKT1.

Inhibition Assay of Cdk2/Cyclin A Activity

Kinase reaction: 1.5 μM histone H1 substrate, 25 μM ATP (0.2 μCi P33 γ-ATP), 30 ng of baculovirus co-expressed Cdk2/Cyclin A, 10 μM inhibitor in a final volume of 100 μl buffer (TRIS HCl 10 mM pH 7.5, $MgCl_2$ 10 mM, 7.5 mM DTT) were added to each well of a 96 U bottom well plate. After 10 min at 37° C. incubation, reaction was stopped by 20 μl EDTA 120 mM.

Capture: 100 μl were transferred from each well to Multi-Screen plate, to allow substrate binding to phosphocellulose filter. Plates were then washed 3 times with 150 μl/well PBS $Ca^{++}/Mg^{++}$ free and filtered by MultiScreen filtration system. Detection: filters were allowed to dry at 37° C., then 100 μl/well scintillant were added and 33P labeled histone H1 was detected by radioactivity counting in the Top-Count instrument.

Results: data were analyzed and expressed as % inhibition referred to total activity of enzyme (=100%).

All compounds showing inhibition ≧50% were further analyzed in order to study and define potency ($IC_{50}$) as well as the kinetic-profile of inhibitor through Ki calculation.

$IC_{50}$ determination: the protocol used was the same described above, where inhibitors were tested at different concentrations ranging from 0.0045 to 10 μM. Experimental data were analyzed by the computer program GraphPad Prizm using the four parameter logistic equation:

$$y = \text{bottom} + (\text{top}-\text{bottom})/(1+10^{((\log IC_{50}-x)*\text{slope})})$$

where x is the logarithm of the inhibitor concentration, y is the response; y starts at bottom and goes to top with a sigmoid shape.

Ki calculation: either the concentration of ATP and histone H1 substrate were varied: 4, 8, 12, 24, 48 μM for ATP (containing proportionally diluted $P^{33}\gamma$-ATP) and 0.4, 0.8, 1.2, 2.4, 4.8 μM for histone were used in absence and presence of two different, properly chosen inhibitor concentrations.

Experimental data were analyzed by the computer program "SigmaPlot" for Ki determination, using a random bireactant system equation:

$$v = \frac{Vmax \frac{(A)(B)}{aKAKB}}{1 + \frac{(A)}{KA} + \frac{(B)}{KB} + \frac{(A)(B)}{aKAKB}}$$

where A=ATP and B=histone H1.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) can be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) can range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which can be a carrier or a diluent.

The pharmaceutical compositions containing the compounds of the invention are usually prepared following conventional methods and are administered in a suitable pharmaceutical form.

For example, the solid oral forms can contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations can be manufactured in known manner, for example, by means of mixing, granulating, tabletting, sugar-coating, or film-coating processes.

The liquid dispersions for oral administration can be, e.g., syrups, emulsions and suspensions.

As an example, the syrups can contain, as carrier, saccharose or saccharose with glycerine and/or mannitol and sorbitol.

The suspensions and the emulsions can contain, as examples of carriers, natural gum, agar, sodium alginate, pectin, methylcellulose, carboxymethylcellulose, or polyvinyl alcohol.

The suspension or solutions for intramuscular injections can contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions can contain, as a carrier, sterile water or preferably they can be in the form of sterile, aqueous, isotonic, saline solutions or they can contain propylene glycol as a carrier.

The suppositories can contain, together with the active compound, a pharmaceutically acceptable carrier, e.g., cocoa butter, polyethylene glycol, a polyoxyethylene sorbitan fatty acid ester surfactant or lecithin.

With the aim to better illustrate the present invention, without posing any limitation to it, the following examples are now given.

GENERAL METHODS

Flash Chromatography was performed on silica gel (Merck grade 9395, 60A). HPLC was performed on Waters X Terra RP 18 (4.6×50 mm, 3.5 µm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was $H_2O$/acetonitrile (5:95). Gradient from 10 to 90% B in 8 minutes, hold 90% B 2 minutes. UV detection at 220 nm and 254 nm. Flow rate 1 ml/min. Injection volume 10 µl. Full scan, mass range from 100 to 800 amu. Capillary voltage was 2.5 KV; source temp. was 120° C.; cone was 10 V. Retention times (HPLC r.t.) are given in minutes at 220 nm or at 254 nm. Mass are given as m/z ratio.

When necessary, compounds have been purified by preparative HPLC on a Waters Symmetry C18 (19×50 mm, 5 um) column using a Waters preparative HPLC 600 equipped with a 996 Waters PDA detector and a Micromass mod. ZMD single quadrupole mass spectrometer, electron spray ionization, positive mode. Mobile phase A was water 0.01% TFA, and Mobile phase B was acetonitrile. Gradient from 10 to 90% B in 8 min, hold 90% B 2 min. Flow rate 20 ml/min.

1H-NMR spectrometry was performed on a Mercury VX 400 operating at 400.45 MHz equipped with a 5 mm double resonance probe [1H (15N-31P) ID_PFG Varian].

The compounds of formula (I), having an asymmetric carbon atom and obtained as racemic mixture, were resolved by HPLC separation on chiral columns. In particular, for example, preparative columns CHIRALPACK® AD can be used.

EXAMPLE 1

2,4-Dioxo-piperidine-1-carboxylic acid tert-butyl ester

Boc-β-alanine (25 g, 132 mmol), Meldrum's acid (20.9 g, 145 mmol) and 4-dimethylaminopyridine (DMAP, 24.2 g, 198 mmol) were dissolved in 700 mL of dry dichloromethane (DCM) at 0° C. under nitrogen atmosphere. To this solution 1-(3-dimethylaminopropyl)-3-ethylcarbodiimide hydrochloride (EDCI, 30.4 g, 158 mmol) was added. The resulting solution was allowed to reach room temperature and stirred overnight. The reaction mixture was washed (0.5 L×4) with 5% KHSO$_4$ aqueous solution. The organic layer was dried over anh. Na$_2$SO$_4$, filtered and evaporated under vacuum, affording crude [3-(2,2-dimethyl-4,6-dioxo-[1,3]dioxan-5-yl)-3-oxo-propyl]-carbamic acid tert-butyl ester that was dissolved in 600 mL of ethylacetate and refluxed for 4 hours. The solvent was reduced to 150 mL under vacuum and the resulting solution was allowed to crystallize at 4° C. overnight. The solid was filtered and washed with cold ethyl acetate affording 18.4 g (65% yield) of the title compound.

$^1$H NMR (400 MHz, DMSO-D6) δ ppm 1.44 (s, 9H) 2.44 (m, 2H) 3.71 (m, 2H) 4.95 (s, 1H) 11.2 (bs, 1H).

The compound thus obtained can be converted into piperidine-2,4-dione in quantitative yield by dissolving it in dichloromethane and treating with trifluoroacetic acid at room temperature for 3 hours.

EXAMPLE 2

Piperidine-2,4-dione

A solution of β-alanine ethylester hydrochloride (13.8 g, 90 mmol) in dichloromethane (90 mL) and triethylamine (TEA, 13.8 mL, 99 mmol) was stirred at room temperature for 1 hour. More TEA (13.8 mL, 99 mmol) was added, the solution was cooled to 0° C. under stirring and ethylmalonylchloride (12.6 mL, 99 mmol) was added dropwise. After 1 hour at 0° C., the reaction mixture was stirred 1 hour at room temperature. A 15% aqueous solution of K$_2$CO$_3$ (90 mL) was added and the layers were separated. The organic phase was washed with 10% HCl (90 mL), dried over Na$_2$SO$_4$, filtered and concentrated under reduced pressure. The crude material was chromatographed on flash silica gel (450 g, eluant: ethyl acetate/n-hexane 2:1) to give N-(2-ethoxycarbonyl-ethyl)-malonamic acid ethyl ester as a yellow oil (15 g, 64.9 mmol, 72% yield). Sodium metal (610 mg, 26.6 mmol) was dissolved in dry MeOH (25 mL) at room temperature under stirring and inert atmosphere. After complete dissolution the mixture was stirred 10' longer, then N-(2-ethoxycarbonyl-ethyl)-malonamic acid ethyl ester (6.15 g, 26.6 mmol) in dry toluene (150 mL) was added dropwise. After addition, the reaction mixture was stirred at 90° C. for 6 hours, cooled to room temperature, water (30 mL) was added and the layers were separated. The organic phase was washed with water (2×10 mL), the combined aqueous phases were acidified with 37% HCl and extracted thoroughly with a mixture of DCM/MeOH (5:1). After drying over Na$_2$SO$_4$ and concentration, 3-methoxycarbonylpiperidin-2,4-dione as a pink solid was obtained (4 g, 88% yield). 3-Methoxycarbonylpiperidin-2,4-dione (4 g, 23.4 mmol) was dissolved in acetonitrile containing 1% of water (250 mL) and refluxed for 4 hours. The reaction mixture was concentrated to give the title compound, as a yellow solid (2.4 g, 90% yield).

$^1$H NMR (400 MHz, DMSO-D6) δ ppm 2.43-2.49 (m, 2H) 3.24 (s, 2H) 3.28-3.45 (m, 2H) 8.07 (s, 1H).

EXAMPLE 3

DL-6-Benzylpiperidine-2,4-dione

A mixture of beta-homophenylalanine (9.1 g, 50.9 mmol), di-tert-butyl dicarbonate (12.2 g, 56 mmol), dioxane (180 mL), water (18 mL) and TEA (8.5 mL) was stirred at room temperature overnight. After concentration and multiple strippings with toluene, 3-[(tert-butoxycarbonyl)amino]-4-phenylbutanoic acid was obtained as an oil and used directly in the next step. It was dissolved in dry dichloromethane (370 mL), Meldrum's acid (8.1 g, 56.1 mmol) and DMAP (9.7 g, 79 mmol) were added to it, the mixture was cooled to −5° C. and dicyclohexylcarbodiimide (12.6 g, 61 mmol) was added. After addition the reaction mixture was kept into the refrigerator overnight. The precipitate was filtered off and washed with dichloromethane. The filtrate was diluted with ethylacetate, washed in sequence with 10% aq KHSO$_4$, water, brine, then concentrated to yield crude tert-butyl 1-benzyl-3-(2,2-dimethyl-4,6-dioxo-1,3-dioxan-5-yl)-3-oxopropylcarbamate that was dissolved in ethylacetate (250 mL) and refluxed for 2 hours. After concentration and treatment with diisopropylether the crystallized compound was filtered and washed with the same solvent to give tert-butyl 2-benzyl-4,6-dioxopiperidine-1-carboxylate as a white powder in 75% overall yield. The title compound was obtained in quantitative yield after acidic treatment (4M HCl in dioxane) at room temperature.

$^1$H NMR (400 MHz, DMSO-D6) δ ppm 2.32 (dd, J=15.73, 8.17 Hz, 1H) 2.42 (dd, J=16.34, 4.76 Hz, 1H) 2.66-2.74 (m, 1H) 2.87-3.02 (m, 2H) 3.25-3.40 (m, 1H) 3.84-3.93 (m, 1H) 7.20-7.36 (m, 5H) 8.14 (s, 1H).

[M+H]$^+$=204

By working in an analogous way as in Example 3, the following compound in Example 4 was also obtained:

EXAMPLE 4

5,5-dimethylpiperidine-2,4-dione $^1$H NMR (400 MHz, DMSO-D6) δ ppm 1.0 (s, 6H) 3.15 (s, 2H) 3.25 (s, 2H) 8.0 (s, 1H).

[M+H]$^+$=142

EXAMPLE 5

4-(Isoquinolin-5-ylamino)-5,6-dihydro-1H-pyridin-2-one

Isoquinolin-5-ylamine (4 g, 27.9 mmol) and piperidine-2,4-dione (4.1 g, 36.2 mmol) were heated at reflux in absolute ethanol (200 mL) with a Dean-Stark apparatus for 3-4 hours. The solvent was concentrated under vacuum and the resulting solid foam, corresponding to the title compound, was dried under vacuum and used in the next step without further purification (4.45 g, yield 67%).

$^1$H NMR (400 MHz, CD3OD) δ ppm 2.76 (t, J=7.95, 2H) 3.48 (t, J=8.01, 2H) 4.58 (s, 1H) 7.73 (m, 2H) 7.89 (d, J=7.89, 1H) 8.03 (m, 1H) 8.48 (d, J=8.04, 1H) 9.28 (s, 1H).

[M+H]$^+$=240

By working in an analogous way as in Example 5, starting from 6-benzylpiperidine-2,4-dione, the following compound in Example 6 was also obtained:

EXAMPLE 6

DL-6-Benzyl-4-(isoquinolin-5-ylamino)-5,6-dihydro-1H-pyridin-2-one $^1$H NMR (400 MHz, DMSO-D6) δ ppm 2.50-2.53 (m, 2H) 2.78 (dd, J=13.05, 8.90 Hz, 1H) 3.00 (dd, J=13.29, 4.88 Hz, 1H) 3.73-3.82 (m, 1H) 4.42 (s, 1H) 6.60 (s, 1H) 7.24-7.39 (m, 5H) 7.62-7.65 (m, 1H) 7.70 (t, J=7.71, 1H) 7.79-7.82 (m, 1H) 7.99 (d, J=8.05 Hz, 1H) 8.51-8.55 (m, 2H) 9.36 (d, J=0.85 Hz, 1H).
$[M+H]^+=330$ By working in an analogous way as in Example 5, starting from cyclohexane-1,3-dione, the following compound in Example 7 was also obtained:

EXAMPLE 7

3-(Isoquinolin-5-ylamino)-cyclohex-2-enone $^1$H NMR (400 MHz, DMSO-D6) δ ppm 1.92-2.01 (m, 2H) 2.18 (t, J=6.46 Hz, 2H) 2.69 (t, J=6.16 Hz, 2H) 4.71 (s, 1H) 7.68 (d, J=6.83 Hz, 1H) 7.74 (t, J=7.65 Hz, 1H) 7.79 (d, J=5.85 Hz, 1H) 8.08 (d, J=8.05 Hz, 1H) 8.56 (d, J=5.97 Hz, 1H) 9.05 (s, 1H) 9.40 (s, 1H).
$[M+H]^+=239$

EXAMPLE 8

DL-9-Benzyl-8,9,10,11-tetrahydro-3,8,1-triaza-benzo[a]fluoren-7-one

DL-6-Benzyl-4-(isoquinolin-5-ylamino)-5,6-dihydro-1H-pyridin-2-one (100 mg, 0.3 mmol) was dissolved in DMF (2 mL) and palladium diacetate (10 mg, 0.044 mmol) and copper diacetate (55 mg, 0.3 mmol) were added. The mixture was heated at 120° C. for 120 minutes. The solvent was removed under vacuum and the residue was treated with water and 30% aqueous ammonia. The resulting suspension was filtered off and the solid was washed with water and diethylether. Purification by flash chromatography, with dichloromethane/methanol 95/05 as eluant, provided a solid product, which was dissolved in methanol and treated with 1.25M HCl in methanol to pH 1. The solvent was removed under vacuum and the residue was treated with diethylether. The resulting solid was filtered, washed with diethylether, and dried under vacuum affording 14 mg (13%) of the title compound as hydrochloric salt.

$^1$H NMR (400 MHz, DMSO-D6) δ ppm 2.88 (dd, J=13.23, 8.72 Hz, 1H) 3.00 (dd, J=16.70, 8.53 Hz, 1H) 3.06-3.13 (m, 1H) 3.07 (d, J=5.37 Hz, 1H) 4.05-4.15 (m, 1H) 7.23-7.40 (m, 5H) 7.48 (s, 1H) 8.13 (d, J=8.78 Hz, 1H) 8.49 (d, J=8.66 Hz, 1H) 8.69 (d, J=6.46 Hz, 1H) 8.73 (d, J=6.47 Hz, 1H) 9.78 (s, 1H) 13.50 (s, 1H).
$[M+H]^+=328$ By working in an analogous way as in Example 8, starting from 3-(isoquinolin-5-ylamino)-cyclohex-2-enone, the following compound in Example 9 was also obtained:

EXAMPLE 9

8,9,10,11-Tetrahydro-pyrido[4,3-a]carbazol-7-one $^1$H NMR (400 MHz, DMSO-D6) δ ppm 2.20-2.29 (m, 2H) 2.59 (t, J=6.95 Hz, 2H) 3.20 (t, J=6.22 Hz, 2H) 8.16 (d, J=8.78 Hz, 1H) 8.54 (d, J=8.66 Hz, 1H) 8.75 (s, 2H) 9.78 (s, 1H) 13.62 (s, 1H).
$[M+H]^+=237$

EXAMPLE 10

N-Benzhydrylidene-N'-isoquinolin-5-yl-hydrazine

To a suspension of 5-bromoisoquinoline (200 mg, 0.96 mmol), benzhydrylidene-hydrazine (189 mg, 0.96 mmol), palladium diacetate (2.2 mg, 0.0096 mmol) and 2,2'-bis(diphenylphosphino)-1,1'-binaphthyl (BINAP, 6 mg, 0.0096 mmol) in dry toluene (1 mL), sodium tert-butoxide (130 mg, 1.34 mmol) was added and the mixture was heated at 85° C. for 4 hours. The mixture, cooled to room temperature, was filtered over celite and the pad was washed with diethylether. The solvent was evaporated under vacuum and the residue was purified by flash chromatography with hexane/ethylacetate 7/3 as eluant, affording 268 mg of the title compound (86% yield).

$^1$H NMR (400 MHz, DMSO-D6) δ ppm 7.35 (d, J=6.10 Hz, 1H) 7.38-7.45 (m, 3H) 7.48-7.52 (m, 2H) 7.57-7.74 (m, 7H) 7.88 (dd, J=7.44, 1.10 Hz, 1H) 8.39 (d, J=5.97 Hz, 1H) 8.76 (s, 1H) 9.24 (s, 1H).
$[M+H]^+=324$

EXAMPLE 11

10,10-Dimethyl-8,9,10,11-tetrahydro-3,8,11-triaza-benzo[a]fluoren-7-one

A mixture of N-benzhydrylidene-N'-isoquinolin-5-yl-hydrazine (154 mg, 0.48 mmol) and 5,5-dimethylpiperidine-2,4-dione (98 mg, 0.69 mmol), dissolved in acetic acid (2 mL) and water (8 drops), was submitted to microwaves for 40 minutes at 150° C. The mixture was treated with concentrated NaOH to pH 9 and was extracted three times with ethyl acetate. Purification by flash chromatography of the concentrated residue, with dichloromethane/methanol/acetic acid/water 30/2/0.5/0.2→30/4/1/0.5 as eluant, afforded a solid product, which was dissolved in methanol and treated with 1.25M HCl in methanol to pH 1. The solvent was removed under vacuum and the residue was treated with diethylether. The resulting solid was filtered, washed with diethylether, and dried under vacuum, affording 72 mg of the title compound as hydrochloric salt (28%).

$^1$H NMR (400 MHz, DMSO-D6) δ ppm 1.49 (s, 6H) 3.30-3.39 (m, 2H) 7.52 (s, 1H) 8.11 (d, J=8.66 Hz, 1H) 8.51 (d, J=8.66 Hz, 1H) 8.76 (d, J=6.58 Hz, 1H) 8.99 (d, J=5.78 Hz, 1H) 9.76 (s, 1H) 13.25 (s, 1H).
$[M+H]^+=266$ By working in an analogous way as in Example 11, starting from 5,5-dimethyl-cyclohexane-1,3-dione, the following compound in Example 12 was also obtained:

EXAMPLE 12

9,9-Dimethyl-8,9,10,11-tetrahydro-pyrido[4,3-a]carbazol-7-one $^1$H NMR (400 MHz, DMSO-D6) δ ppm 1.17 (s, 6H) 2.51 (s, 2H) 3.12 (s, 2H) 8.19 (d, J=8.68 Hz, 1H) 8.54 (d, J=8.68 Hz, 1H) 8.78 (d, J=6.70 Hz, 1H) 8.88 (d, J=6.70 Hz, 1H) 9.82 (s, 1H) 13.87 (s, 1H).
$[M+H]^+=265$

EXAMPLE 13

11-(2,2,2-Trifluoro-ethyl)-8,9,10,11-tetrahydro-3,8,11-triaza-benzo[a]fluoren-7-one 4.45 g (18.6 mmol) of 4-(isoquinolin-5-ylamino)-5,6-dihydro-1H-pyridin-2-one were dissolved in DMF (10 mL) and palladium diacetate (445 mg, 1.98 mmol) and copper diacetate (3.39 g, 18.7 mmol) were added. The mixture was heated at 120° C. for 90 minutes; then more palladium diacetate (220 mg) and copper diacetate (1.7 g) were added and the heating was continued 30 minutes longer. The solvent was removed under vacuum and the residue was treated with water and 30% aqueous ammonia. The resulting suspension was filtered off and the solid was washed with water and diethylether. Purification by flash chromatography with dichloromethane/methanol/acetic acid/water 80/20/7/3 as eluent gave a solid product, which was dissolved in methanol and treated with 1.25M HCl in methanol to pH 1. The solvent was removed under vacuum and the residue was treated with diethylether. The resulting solid was filtered, washed with diethylether and dried under vacuum, affording 760 mg (15%) of 8,9,10,11-tetrahydro-3,8,11'-triaza-benzo[a]fluoren-7-one hydrochloride.

$^1$H NMR (400 MHz, DMSO-D6) δ ppm 3.19 (t, J=6.85 Hz, 2H) 3.54-3.59 (m, 2H) 7.43 (s, 1H) 8.10 (d, J=8.68 Hz, 1H) 8.47 (d, J=8.83 Hz, 1H) 8.71 (d, J=6.55 Hz, 1H) 8.79 (d, J=6.55 Hz, 1H) 9.76 (s, 1H) 13.69 (s, 1H).

A mixture of 8,9,10,11-tetrahydro-3,8,11-triaza-benzo[a]fluoren-7-one (213 mg, 0.9 mmol), trifluoro-methanesulfonic acid 2,2,2-trifluoro-ethyl ester (317 mg, 1.35 mmol), potassium carbonate (253 mg, 1.8 mmol) and 18-crown-6 ether (481 mg, 1.8 mmol) in anhydrous DMF (20 mL) was stirred under heating at 65° C. for 3 hours. More trifluoro-methanesulfonic acid 2,2,2-trifluoro-ethyl ester (200 mg, 0.86 mmol), potassium carbonate (253 mg, 1.8 mmol) and 18-crown-6 (240 mg, 0.9 mmol) were added and heating continued for 3 hours. After cooling, the solvent was evaporated under vacuum and the crude product was purified by flash chromatography with DCM/MeOH 95:5 as eluant, affording a solid product. The solid product was then dissolved in methanol and treated with 1.25M HCl in methanol to pH 1. The solvent was removed under vacuum and the residue was treated with diethylether. The resulting solid was filtered, washed with diethylether, and dried under vacuum, affording 127 mg of the title compound as hydrochloric salt (39% yield).

$^1$H NMR (400 MHz, DMSO-D6) δ ppm 3.26 (t, J=6.83 Hz, 2H) 3.57-3.64 (m, 2H) 5.91 (q, J=8.86 Hz, 2H) 7.68 (s, 1H) 8.24 (d, J=8.78 Hz, 1H) 8.66 (d, J=8.66 Hz, 1H) 8.72 (d, J=6.83 Hz, 1H) 8.89 (d, J=6.95 Hz, 1H) 9.81 (s, 1H). [M+H]$^+$=320

By working in an analogous way as in Example 13, starting from 8,9,10,11-tetrahydro-pyrido[4,3-a]carbazol-7-one, the following compound in Example 14 was also obtained:

EXAMPLE 14

11-(2,2,2-Trifluoro-ethyl)-8,9,10,11-tetrahydro-pyrido[4,3-a]carbazol-7-one $^1$H NMR (400 MHz, DMSO-D6) δ ppm 2.18-2.28 (m, 2H) 2.60 (t, J=6.45 Hz, 2H) 3.21 (t, J=6.04 Hz, 2H) 5.88 (q, J=8.66 Hz, 2H) 8.20 (d, J=8.66 Hz, 1H) 8.64 (d, J=8.66 Hz, 1H) 8.69 (d, J=6.71 Hz, 1H) 8.75 (d, J=6.95 Hz, 1H) 9.69 (s, 1H). [M+H]$^+$=319

Based on the methods described above, the following compounds were also synthesized:
10-(3,3,3-Trifluoro-propyl)-8,9,10,11-tetrahydro-3,8,11-triaza-benzo[a]fluoren-7-one;
10-(2-Fluoro-ethyl)-8,9,10,11-tetrahydro-3,8,11-triaza-benzo[a]fluoren-7-one;
10-Cyclobutyl-8,9,10,11-tetrahydro-3,8,11-triaza-benzo[a]fluoren-7-one;
10-Ethyl-8,9,10,11-tetrahydro-3,8,11-triaza-benzo[a]fluoren-7-one;
9-Cyclopropyl-8,9,10,11-tetrahydro-3,8,11-triaza-benzo[a]fluoren-7-one; and
9-Cyclopropyl-11-(2,2,2-trifluoro-ethyl)-8,9,10,11-tetrahydro-3,8,11-triaza-benzo[a]fluoren-7-one.

It is to be understood that many modifications and variations may be devised given the above description of the principles of the invention. It is intended that all such modifications and variations can be considered as within the spirit and scope of this invention, as it is defined in the following claims.

We claim:
1. A compound represented by formula (I)

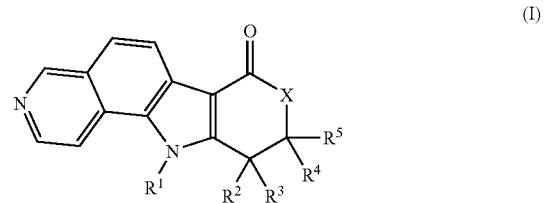

(I)

wherein
R$^1$ is selected from the group consisting of hydrogen, (C$_1$-C$_6$)alkyl, (C$_2$-C$_6$)alkenyl, (C$_2$-C$_6$)alkynyl, (C$_3$-C$_6$)cycloalkyl, (C$_1$-C$_6$)haloalkyl, (C$_1$-C$_6$)polyfluorinated alkyl, heterocyclyl, aryl, heteroaryl, (C$_3$-C$_6$)cycloalkyl-(C$_1$-C$_6$)alkyl, heterocyclyl-(C$_1$-C$_6$)alkyl, aryl-(C$_1$-C$_6$)alkyl, heteroaryl-(C$_1$-C$_6$)alkyl, (C$_1$-C$_8$)hydroxyalkyl, (C$_1$-C$_8$)alkoxy-(C$_1$-C$_8$)alkyl, aryloxy-(C$_1$-C$_8$)alkyl, heteroaryloxy-(C$_1$-C$_8$)alkyl, (C$_1$-C$_8$)aminoalkyl, (C$_1$-C$_8$)alkylamino-(C$_1$-C$_8$)alkyl, (C$_1$-C$_8$)dialkylamino-(C$_1$-C$_8$)alkyl, carbamoyl-(C$_1$-C$_8$)alkyl, and alkoxycarbonyl, wherein each of said aryl, heteroaryl, heterocyclyl, aryloxy, or heteroaryloxy moieties can be unsubstituted or substituted by one or more substituents, each substituent being independently selected from the group consisting of alkyl, aryl, —OCF$_3$, —OC(O)alkyl, —OC(O)aryl, —CF$_3$, heteroaryl, aralkyl, alkylaryl, heteroaralkyl, alkylheteroaryl, hydroxy, hydroxyalkyl, alkoxy, aryloxy, aralkoxy, acyl, aryl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, heterocyclyl, heterocyclenyl, —NH(alkyl), —NH(cycloalkyl), and —N(alkyl)$_2$;

R$^2$, R$^3$, R$^4$ and R$^5$ are each independently selected from the group consisting of hydrogen atom, (C$_1$-C$_6$)alkyl, (C$_3$-C$_6$)cycloalkyl, heterocyclyl, aryl, cycloalkyl-alkyl, heterocyclyl-(C$_1$-C$_6$)alkyl, aryl-(C$_1$-C$_6$)alkyl, (C$_1$-C$_6$)haloalkyl, (C$_1$-C$_6$)polyfluorinated alkyl, (C$_1$-C$_8$)hydroxyalkyl, (C$_1$-C$_8$)alkoxy-(C$_1$-C$_8$)alkyl, aryloxy (C$_1$-C$_8$)alkyl, heteroaryloxy(C$_1$-C$_8$)alkyl, (C$_1$-C$_8$)aminoalkyl, (C$_1$-C$_8$)alkylamino(C$_1$-C$_8$)alkyl, and (C$_1$-C$_8$)dialkylamino-(C$_1$-C$_8$)alkyl,
or R$^2$, R$^3$, R$^4$ and R$^5$, taken together, form a (C$_3$-C$_6$)cycloalkyl group;
X is NH or CH$_2$,
with the provisos that,
when X is NH and R$^1$ is hydrogen atom, at least one of R$^2$, R$^3$, R$^4$ and R$^5$ is not a hydrogen atom and 7H-pyrido[4,3-a]carbazol-7-one, 8,9,10,11-tetrahydro-11-(phenylmethyl) is excluded;
or a pharmaceutically acceptable salt thereof.

2. The compound according to claim 1, wherein R$^4$ and R$^5$ are hydrogen atoms.

3. The compound according to claim 1, wherein $R^2$ and $R^3$ are hydrogen atoms.

4. The compound according to claim 1, wherein $R^1$, $R^2$, $R^3$ and $R^4$ are hydrogen atoms.

5. The compound according to claim 1, wherein $R^1$, $R^2$, $R^3$ and $R^5$ are hydrogen atoms.

6. The compound according to claim 1, wherein X is NH, and $R^1$, $R^2$, $R^4$ and $R^5$ are hydrogen atoms.

7. A compound according to claim 1 selected from the group consisting of:
   DL-9-Benzyl-8,9,10,11-tetrahydro-3,8,11-triaza-benzo [a]fluoren-7-one;
   8,9,10,11-Tetrahydro-pyrido [4,3 -a] carbazol-7-one;
   10,10-Dimethyl-8,9,10,11-tetrahydro-3,8,11-triaza-benzo [a]fluoren-7-one;
   9,9-Dimethyl-8,9,10,11-tetrahydro-pyrido [4,3 -a] carbazol-7-one;
   11-(2,2,2-Trifluoro-ethyl)-8,9,10,11-tetrahydro-3,8,11-triaza-benzo [a] fluoren-7-one;
   11-(2,2,2-Trifluoro-ethyl)-8,9,10,11-tetrahydro-pyrido [4,3 -a] carbazol-7-one;
   10-(3,3,3-Trifluoro-propyl)-8,9,10,11-tetrahydro-3,8,11-triaza-benzo [a]fluoren-7-one;
   10-(2-Fluoro-ethyl)-8,9,10,11-tetrahydro-3,8,11-triaza-benzo[a]fluoren-7-one;
   10-Cyclobutyl-8,9,10,11-tetrahydro-3,8,11-triaza-benzo [a]fluoren-7-one;
   10-Ethyl-8,9,10,11-tetrahydro-3,8,11-triaza-benzo [a] fluoren-7-one;
   9-Cyclopropyl-8,9,10,11-tetrahydro-3,8,11-triaza-benzo [a]fluoren-7-one; and
   9-Cyclopropyl- 11-(2,2,2-trifluoro-ethyl)-8,9,10,11-tetrahydro-3, 8,11-triaza-benzo [a]fluoren-7-one.

8. A pharmaceutical composition comprising an amount of the compound according to claim 1, or a pharmaceutically acceptable salt thereof, and a pharmaceutically acceptable carrier.

9. A method of antagonizing activity toward Cdk2 or Cdc7, comprising administering to said Cdk2 or Cdc7 an amount of a compound of claim 1 that is effective in antagonizing activity toward Cdk2 or Cdc7.

10. A method of treating a disorder or condition selected from the group consisting of head and neck cancers, mesothelioma, renal cancer, testicular cancer, breast cancer, colon cancer, kidney cancer, non-small cell lung cancer, esophagus cancer, pancreatic cancer, gastric cancer, cervical cancer, prostate cancer, mantle cell lymphoma, Hodgkin's disease, non-Hodgkin's lymphoma, anaplastic large cell lymphoma, acute and chronic myelogenous leukemias, melanoma, soft-tissue sarcoma, thymoma, osteosarcoma, in a mammal, comprising administering to said mammal in need of said treatment an amount of a compound of according to claim 1 that is effective in treating said condition or disorder.

11. A method of treating a disorder or condition selected from the group consisting of head and neck cancers, mesothelioma, renal cancer, testicular cancer, breast cancer, colon cancer, kidney cancer, non-small cell lung cancer, esophagus cancer, pancreatic cancer, gastric cancer, cervical cancer, prostate cancer, mantle cell lymphoma, Hodgkin's disease, non-Hodgkin's lymphoma, anaplastic large cell lymphoma, acute and chronic myelogenous leukemias, melanoma, soft-tissue sarcoma, thymoma, osteosarcoma, in a mammal, comprising administering to said mammal in need of said treatment an amount of a compound according to claim 1 that is effective in antagonizing activity toward Cdk2 or Cdc7.

12. The method according to claim 10, wherein said cancer is selected melanomaoma and osteosarcoma.

13. The method according to claim 11, wherein said cancer is selected from the group consisting of melanoma, and osteosarcoma.

* * * * *